United States Patent [19]

Zupancic et al.

[11] 4,162,364

[45] Jul. 24, 1979

[54] PROCESS FOR THE PREPARATION OF 2-(3-BENZOYLPHENYL)-PROPIONIC ACID

[75] Inventors: Boris Zupančič, Ljubljana; Branko Jenko, Ljubljana-Polje, both of Yugoslavia

[73] Assignee: LEK Tovarna farmacevtskih in kemičnih izdelkov, n.sol.o., Ljubljana, Yugoslavia

[21] Appl. No.: 842,822

[22] Filed: Oct. 17, 1977

[30] Foreign Application Priority Data

Oct. 18, 1976 [YU] Yugoslavia .......................... 2547/76

[51] Int. Cl.$^2$ ...................... C07C 51/24; C07C 51/33
[52] U.S. Cl. ...................................... 562/408; 560/52; 562/409

[58] Field of Search ................... 562/408, 409; 560/52

[56] References Cited

U.S. PATENT DOCUMENTS 3,828,093   8/1974   Bays et al. .............................. 560/52

*Primary Examiner*—Paul J. Killos
*Attorney, Agent, or Firm*—Pollock, Vande Sande & Priddy

[57] ABSTRACT

A process for preparing 2-(3-benzoylphenyl)-propionic acid which includes treating 1-(3-benzoylphenyl)-propine with a thallium (III) salt in a lower alkanol to obtain 2-(3-benzoylphenyl)-propionic ester, and hydrolyzing the ester.

13 Claims, No Drawings

PROCESS FOR THE PREPARATION OF 2-(3-BENZOYLPHENYL)-PROPIONIC ACID

The present invention relates to a new process for the preparation of 2-(3-benzoylphenyl)-propionic acid of the formula

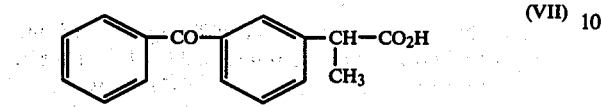

a compound possessing a significant antiinflammatory activity, which comprises treating 1-(3-benzoylphenyl)-propine with a thallium(III) salt, like thallium(III) nitrate, in a lower alkanol in order to form the corresponding 2-(3-benzoylphenyl)-propionic ester which is hydrolyzed.

The new process is illustrated by the following scheme:

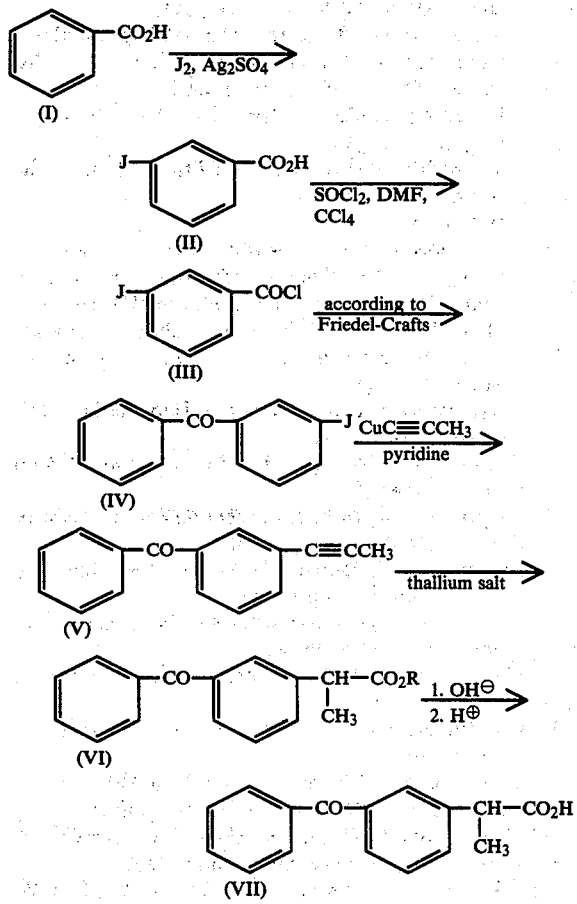

In the scheme R stands for a lower alkyl containing 1 to 4 carbon atoms, preferably for methyl and ethyl.

Besides the easily available benzoic acid, 3-aminobenzoic acid may be used as the starting substance, whereupon the intermediary diazotate is iodinated. Instead of silver sulfate there may be used lead sulfate as well, thus further reducing the costs of the synthesis.

Besides the disclosed reaction sequence, there is also feasible the following one, leading to 1-(3-benzoylphenyl)-propine over the formation of 3-bromo benzophenone:

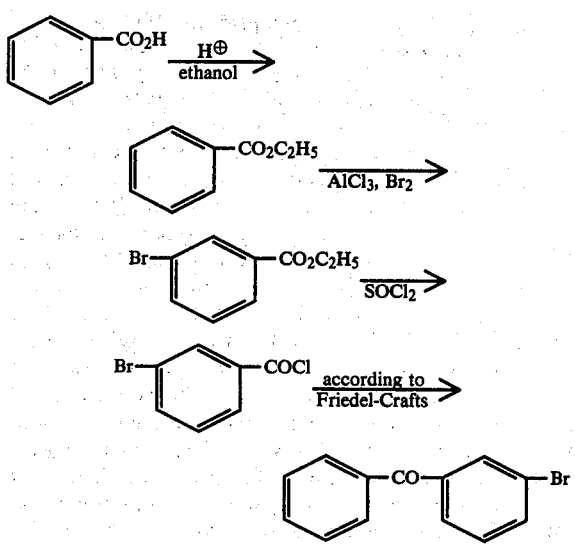

The latter may also be converted into the desired final compound under somewhat severer reaction conditions.

1-(3-Benzoylphenyl)-propine may also be obtained starting from 3-bromo propiophenone over the formation of 3-(1-chloro-1-propenyl) benzophenone, yielded at the treatment of 3-(1-oxopropyl) benzophenone with $PCl_5$ in an aprotic solvent. The dehalogenation of 3-(1-chloro-1-propenyl) benzophenone by means of sodium methoxide yields the 1-(3-benzoylphenyl) propine. It is understood that in the latter case the reaction is protracted for some steps, thus considerably impairing the technological as well as the economical aspect of the process.

1-(3-Benzoylphenyl) propine, obtained in accordance with any of the above methods, is converted into the final compound by means of a thallium(III) salt, e.g. thallium(III) nitrate, in a lower alkanol and at a temperature of 0° to 60° C., normally at ambient temperature. The reaction is performed in 0.5 to 2 hours.

In this application the term lower alkanol denotes aliphatic alcohols containing 1 to 4 carbon atoms, also combined with each other or with some halogenated hydrocarbons like chloroform or dichloromethane. The reaction is most advantageously performed in an excess of methanol or ethanol.

The ester obtained at this step is subsequently hydrolyzed, either with a strong base or a strong acid, the required time of reaction being max. 24 hours at a minimum temperature of 50° C. The resulting crude 2-(3-benzoylphenyl)-propionic acid is purified in a conventional manner, e.g. by dissolving in a suitable solvent like acetic acid, followed by dilution with water and filtration or precipitation (e.g. with a diluted mineral acid after the alkali hydrolysis), whereupon the crystallization is performed from acetonitrile or a mixture of petroleum ether/benzene or acetone/water.

The purification may also be performed by means of chromatographic methods and/or fractionating precipitation. The invention is illustrated by the following Examples:

EXAMPLE 1

3-(1-propinyl) benzophenone (V)

An autoclave of 200 ml., equipped with a heater and a stirrer, is charged with 26.6 g. of 3-iodo-benzophenone, m.p. 38.5° to 42.5° C., lit. 44° C. (B. V. Trunov, E. S. Novikova, Žur. obšč. himii 26, 1994 (1956)), 8.9 g. of Cu-propine (W. R. Pilgrim's Ph.D. Thesis, p. 47, Queen's University, Kingston, Ontario, Canada, March 1969), and 80 ml. of pyridine, whereupon it is evacuated seven times and charged with nitrogen. Finally the autoclave with the nitrogen atmosphere is closed. Under stirring the reaction mixture is heated to 110° to 120° C. and after 17 hours it is cooled down to ambient temperature and poured into 500 ml. of water. The precipitated CuI is filtered off and washed with 200 ml. of ether. In a separating funnel the aqueous layer is separated and extracted with two 150 ml.-portions of ether. The combined ether extracts are washed with two 75 ml.-portions of 5% w./w. HCl and then with four 75 ml.-portions of water. The product is dried over $Na_2SO_4$, filtered and transferred into a distillation apparatus. The main fraction distills over at 185° to 196° C./0.4 mm. Hg.

Yield: 16.0 (84.3% theor.), gas chromatography 97%.

Analysis: $C_{16}H_{12}O=220.10$; Calculated: C 87.30 H 5.46: Found: C 86.86 H 5.38.

IR: $\nu/C\equiv/=2240$ cm$^{-1}$ $\nu/CO/=1670$ cm$^{-1}$ n m r: $\delta/$—$CH_3/:2.40/s/$ $\delta/9$ H/:7.96/m/

Methyl-2-(3-benzoylphenyl)-propionate (VI)

35.0 g. of distilled 1-(3-benzoylphenyl) propine (V) are dissolved in 346 ml. of methanol (four-necked reaction flask of 1 l., equipped with a reflux cooler) and there are added 66.8 g. of thallium(III) nitrate trihydrate and the mixture is stirred for 2 hours under refluxing (heating pad). After 2 hours the reaction mixture is cooled down, the precipitated Tl(I)—$NO_3$ is filtered off, diluted with 1020 ml. of water and extracted with four 300 ml.-portions of ether. The ether extracts are washed twice with 200 ml. of water, with 200 ml. of 5% w./w. $NaHCO_3$, once more with 200 ml. of water and finally dried over $Na_2SO_4$. After the separation of $Na_2SO_4$, the filtrate is evaporated to dryness (rotation evaporator). There are obtained 42.0 g. (98.5% theor.) of the product in the form of a bright yellow oil.

Analysis: 87.7% (gas chromatography).

The obtained ester (VI) is distilled over at 0.5 mm. Hg within the range of 197° to 208° C.

Yield: 34.07 g. (80% theor.) of a light yellow oil.

2-(3-benzoylphenyl)-propionic acid

The obtained ester (VI–7.5 g.) is dissolved in 75 ml. of ethanol and, under stirring, 3.75 g. of KOH are added. The mixture is stirred for further three hours at ambient temperature and evaporated on a rotation evaporator. The residue is dissolved in 30 ml. of water and extracted with two 10 ml.-portions of chloroform. The aqueous layer is stirred for 15 minutes with 0.8 g. of active carbon and, after the separation of the carbon, it is acidified by means of 5% w./w. HCl. The resinous product is extracted with two 70 ml.-portions of ether and washed with two 50 ml. portions of water. After the drying of the ether extract over $Na_2SO_4$, it is evaporated to dryness on a rotation evaporator. Yield: 6.0 g. of a resinous product (84.3% theor.), which is crystallized from acetonitrile.

Analysis: m.p. of 93° to 94° C. (Kofler) thin-layer chromatography:impurities in traces contents of the product (titrimetric): exceeding 99.5%

EXAMPLE 2

An autoclave of 200 ml. is successively charged with 26.6 g. of 3-bromo benzophenone, 10.3 g. of Cu-propine and 80 ml. of pyridine (dried over NaOH), evacuated seven times and charged with nitrogen. Finally, the autoclave with the nitrogen atmosphere is closed and heated under stirring to 230° C., whereby the pressure increases to about 15 atm. After 48 hours of stirring at the cited temperature, the reaction mixture is cooled down and poured into 500 ml. of water. The precipitated CuBr is filtered off and washed with 200 ml. of ether. The equeous layer is extracted with two 150 ml.-portions of ether, and the combined ether extracts are washed with two 150 ml.-portions of 5% w./w. HCl. After washing with three 150 mol.-portions of water, the product is dried over $Na_2SO_4$.

$Na_2SO_4$ is filtered off and the ether is evaporated in a rotation evaporator, whereupon the residual oil is distilled over at 185° to 196° C./0.4 mm. Hg.

Yield: 18.0 g. (80.2% theor.) Analysis: thin-layer chromatography: 1 spot

Further on the synthesis is performed in the same way as stated in Example 1.

What is claimed is:

1. A process for the preparation of 2-(3-benzoylphenyl)-propionic acid which comprises treating 1-(3-benzoylphenyl)-propine with a thallium(III) salt in a lower alkanol to form 2-(3-benzoylphenyl)-propionic ester; and hydrolyzing said ester to form 2-(3-benzoylphenyl)-propionic acid.

2. The process of claim 1 wherein said thallium(III) salt is thallium(III) nitrate.

3. The process of claim 1 wherein said lower alkanol is methanol or ethanol.

4. The process of claim 3 wherein an excess quantity of said lower alcohol is employed.

5. The process of claim 1 wherein an excess quantity of said lower alkanol is employed.

6. The process of claim 1 wherein said alkanol contains from 1 to 4 carbon atoms.

7. The process of claim 1 wherein the temperature is from 0° to 60° C.

8. The process of claim 7 wherein said temperature is ambient temperature.

9. The process of claim 1 wherein a halogenated hydrocarbon is also employed in the treating step.

10. The process of claim 9 wherein said halogenated hydrocarbon is chloroform or dichloromethane.

11. The process of claim 1 wherein a strong base or strong acid is employed for hydrolyzing said ester.

12. The process of claim 1 wherein the hydrolyzing is conducted at a temperature of at least 50° C.

13. The process of claim 1 wherein said acid is purified.

* * * * *